US009175019B2

(12) United States Patent
Callens et al.

(10) Patent No.: US 9,175,019 B2
(45) Date of Patent: Nov. 3, 2015

(54) INDUSTRIAL PROCESS FOR THE PREPARATION OF N-ALKYL-N-TRIALKYLSILYLAMIDES

(75) Inventors: Roland Callens, Tielt (BE); Andre Collin, Brussels (BE)

(73) Assignee: PEPTISYNTHA SA, Brussels (BE)

(*) Notice: Subject to any disclaimer, the term of this patent is extended or adjusted under 35 U.S.C. 154(b) by 0 days.

(21) Appl. No.: 14/009,831

(22) PCT Filed: Apr. 2, 2012

(86) PCT No.: PCT/EP2012/055947
§ 371 (c)(1),
(2), (4) Date: Oct. 4, 2013

(87) PCT Pub. No.: WO2012/136617
PCT Pub. Date: Oct. 11, 2012

(65) Prior Publication Data
US 2014/0024805 A1    Jan. 23, 2014

(30) Foreign Application Priority Data

Apr. 5, 2011    (EP) .................................. 11161122

(51) Int. Cl.
*A61K 38/00* (2006.01)
*C07K 1/00* (2006.01)
*C07F 7/08* (2006.01)
*C07F 7/10* (2006.01)
*C07K 1/107* (2006.01)

(52) U.S. Cl.
CPC .................. *C07F 7/0801* (2013.01); *C07F 7/10* (2013.01); *C07K 1/1077* (2013.01)

(58) Field of Classification Search
CPC ....... C07D 471/04; C07K 5/0827; C07K 7/02
See application file for complete search history.

(56) References Cited

U.S. PATENT DOCUMENTS

| 2,876,209 | A | 3/1959 | De Benneville et al. |
| 2,876,234 | A | 3/1959 | Hurwitz |
| 3,903,046 | A | 9/1975 | Greber et al. |
| 4,276,423 | A | 6/1981 | Mueller et al. |
| 4,467,037 | A | 8/1984 | Mawhinney et al. |
| 2010/0298537 | A1* | 11/2010 | Callens et al. ................ 530/337 |

FOREIGN PATENT DOCUMENTS

| EP | 0021238 A1 | 1/1981 |
| EP | 2060580 A1 | 5/2009 |
| EP | 2062909 A1 | 5/2009 |
| JP | H04187673 A | 7/1992 |

OTHER PUBLICATIONS

Mawhinney et al., J. Org. Chem., ACS, 1982, vol. 47, No. 17, pp. 3336-3339.*

Hultin, A Guide to Solvents and Reagents in Introductory Organic Chemistry for students in 2.222, Feb. 2002, available online at: http://home.cc.umanitoba.ca/~hultin/chem2220/Support/solvents_and_reagents.pdf.*

Shitara, K, et al., "Synthesis of heterocyclic compounds containing germanium and nitrogen as hetero-atoms", Journal of Organometallic Chemistry, vol. 346, 1988, pp. 1-6, XP002645103.

C.H. Yoder, et al., "The Structure of Trimethylsilyl Amides", Journal of the American Chemical Society, vol. 96, No. 13,1974, pp. 4283-4286, XP002645104.

Lasocki, Z., et al., "Rate Studies of Silylation With Silylamides", Journal of Organometallic Chemistry, vol. 152, 1978, pp. 45-52, XP002645101.

Mejdi, H., et al., "Studies on Pyrrolidinones. Synthesis of 1-[(N-Acetylaryl-amino) methyl] pyroglutamic Acid Derivatives", vol. 35, 1998, Journal of Heterocyclic Chemistry, pp. 555-565, XP002645102.

Mawhinney, T. P., et al., "N-Methyl-N-(tert-butyldimethylsilyl) trifluoroacetamide and Related N-tert-Butyldimethylsilyl Amides as Protective Silyl Donors", Journal of Organic Chemistry, American Chemical Society, vol. 47, No. 17, Jan. 1, 1982, pp. 3336-3339, XP002995462, ISSN: 0022-3263, DOI: DOI:10.1021/J000138A032.

T.R. Bailey, "Product Class 12: Metal Amides and Imides", Jan. 1, 2005, Science of Synthesis; [Methods of Molecular Transformations. (Houben-Weyl)], Stuttgart: Georg Thieme Verlag, DE, vol. 12, pp. 811-831, XP009149074.

Frainnet, Emille, et al., "Chimie Organique.—Derives silicies de cetoximes.", Comptes Rendus des Seances de L'Academie des Sciences, Serie C: Sciences Chimiques, Jun. 13, 1966, vol. 262, No. 24, pp. 1693-1696.

I.F. Lutsenko, et al., "Interaction of Ketene With Silylated Amines or Amides", Journal of Organometallic Chemistry, vol. 17,1969, pp. 241-262.

A. Kormoriya, et al., "Hindered Rotation in Trimethylsilyl Amides", Journal of the American Chemical Society, 1972, 94:15, pp. 5285-5288.

Fedotov, N.S., et al., "Synthesis of Organic and Organosilicon Nitriles With the Aid of 1, 1, 1, 3, 3, 3-Hexamethyldisilazane", Zhurnal Obshchei Khimii, vol. 42, No. 2, pp. 358-363, Feb. 1972.

Yamamoto, Yutaka, et al., "Studies on Organometallic Compounds. I. Insertion Reaction of Diketene into N-Si Bond of Silylated Amides", Chemical & Pharmaceutical Bulletin, vol. 24, No. 6, 1976, pp. 1236-1241.

Esker John L., et al., "N-Acyl-N-Alkylcarbamoyloxy Radicals: Entries to Amidyl Radicals by Decarboxylation and to a-Amide Radicals by Radical Translocation", Tetrahedron Letters (1992), vol. 33, No. 40, pp. 5913-5916.

Esker, John L., et al., "Multiple Reaction Channels of (N-Acyl-N-alkylcarbamoyl)oxyl Radicals from N-Acyl PTOC Carbamates", J Org. Chem., 1994, vol. 59, pp. 2779-2786.

* cited by examiner

*Primary Examiner* — Marcela M Cordero Garcia
*Assistant Examiner* — Kaipeen Yang
(74) *Attorney, Agent, or Firm* — Mayer Brown LLP

(57)    ABSTRACT

The present invention relates to a process for producing N-alkyl-N-trialkylsilylamides from trialkylsilylhalides and N-alkylamides in the presence of a base and in the absence of a solvent.

18 Claims, No Drawings

INDUSTRIAL PROCESS FOR THE PREPARATION OF N-ALKYL-N-TRIALKYLSILYLAMIDES

CROSS-REFERENCE TO RELATED APPLICATIONS

This application is a U.S. national phase entry under 35 U.S.C. §371 of International Application No. PCT/EP2012/055947, filed on Apr. 2, 2012, which claims priority to European application No. 11161122.4 filed on Apr. 5, 2011, the whole content of this application being incorporated herein by reference for all purposes.

TECHNICAL FIELD OF THE INVENTION

The present invention relates to a process for the preparation of N-alkyl-N-trialkylsilylamides.

BACKGROUND OF THE INVENTION

The N-alkyl-N-trialkylsilylamides are particularly useful as silylating agents in a process for the manufacture of a peptide or peptide analogue. In particular, N-alkyl-N-trialkylsilylamides are useful as silylating agents for amino acids, peptides or peptide analogues in the manufacture of peptides or peptide analogues as e.g. described in EP 2062909 A1 or EP 2060580 A1 or for derivatization of compounds for e.g. gas chromatography as disclosed in U.S. Pat. No. 4,467,037 due to their increased volatility upon silylation.

Different processes for synthesis of N-alkyl-N-trialkylsilylamides are known and summarized e.g. in T. R. Bailey, Science of Synthesis (2005), 21, 811-31. This document discloses the synthesis of 2,2,2-trifluoro-N-methyl-N-(tert-butyldimethylsilyl)acetamide by deprotonating of the amide with NaH at 0° C. followed by treatment with tert-butyldimethylsilyl chloride in a polar aprotic solvent (acetonitrile/benzene 1:1) at 4° C. Further the silylation of N-methylacetamide with trimethylsilyl chloride using triethylamine as nitrogen containing organic base in anhydrous benzene (anhydrous toluene or acetonitrile may be substituted) with the reaction being performed at 0-5° C. is disclosed. The above reactions are explained in more detail in Mahwhinney, T. P.; Madson, M. A., J. Org. Chem., (1982) 47, 3336) and de Benneville, P. L.; Hurwitz, M. J., U.S. Pat. No. 2,876,209, (1959); Chem. Abstr., (1959) 53, 67817.

U.S. Pat. No. 4,467,037 relates to the silylation of amino acids for analysis by gas chromatography. One example of this document discloses the reaction of tert-butyldimethylsilyl chloride (1.3 mole) with N-methylacetamide (1 mole) dissolved in triethylamine, which is used as solvent in an amount of about 10 moles. The reaction mixture is stirred for 24 h at room temperature before isolating the end product.

All of these processes of the prior art have in common that solvents are used for dissolving the educts of the reaction, be it for example acetonitrile/benzene 1:1, anhydrous benzene (or anhydrous toluene or acetonitrile) or triethylamine. These solvents have to be removed at some point during the process to isolate the desired product. The use of solvents is always impaired with costs and environmental burden. Furthermore, if the boiling points of the desired product and the employed solvents are not sufficiently distinct a separation by distillation can additionally complicate the isolation of the desired product.

In another approach for the synthesis of N-methyl-N-trimethysilylacetamide EP 0 021 238 directly heats N-methylacetamide with N-trimethylsilylimidazole to boiling at 13 mbar. The temperature of this process is between 120 and 170° C. and the reaction product is continuously removed by distillation over 8 h. The resulting N-methyl-N-trimethylsilylacetamide is subsequently further purified by fractional distillation. This process requires N-trimethylsilylimidazole which is costly, even when imidazole obtained from the process is recovered and the imidazole is again converted into N-trimethylsilylimidazole, for example by means of hexamethyldisilazane. Furthermore, the process requires long reaction times, which is disadvantageous. Besides, it is difficult to carry out a process using such low pressure in an industrial scale and cleaning of the reaction container containing the imidazole obtained from the process is impeded by the high melting point of imidazole (86-90° C.).

There is need for a process for producing N-alkyl-N-trialkylsilylamides which does not have the disadvantages of the prior art. In particular, the process should be economic and environmentally friendly, even on an industrial scale and be able to provide N-alkyl-N-trialkylsilylamides in a good yield and with a sufficient purity using as few steps as possible while keeping low reaction time and low reaction temperatures.

For solving these problems, the present invention provides a process as defined in the claims.

SUMMARY OF THE INVENTION

It has been found that efficient and economic industrial scale synthesis of N-alkyl-N-trialkylsilylamides of formula I

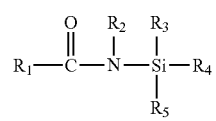

wherein $R_1$ to $R_5$ independently of each other represent a $C_1$-$C_6$ alkyl group, which allows for good results in terms of productivity and purity, can be performed when reacting an N-alkyl amide of formula II

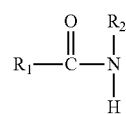

with a compound of formula III

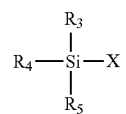

wherein X represents a halogen in the presence of an organic base which is here designated as [OB]. The process of the present invention uses the well known and inexpensive trialkylsilylhalides of formula III for the synthesis of N-alkyl-N-trialkylsilylamides and does not need any solvent. The synthesis of N-alkyl-N-trialkylsilylamides is thus performed in a reaction medium wherein at least 90% of the reaction medium consists of the compound of formula II, the compound of formula III, the organic base [OB] and the reaction products formed during the reaction. Preferably, at least 95%, more preferably at least 98% of the reaction medium consists of the compound of formula II, the compound of formula III, the organic base [OB] and the reaction products formed during the reaction. Most preferably, the reaction medium consists entirely of the above constituents (and usual impurities and by-products of those compounds). Contrary to the processes of the prior art, no solvent is used in the process of the present invention.

DETAILED DESCRIPTION

In this specification, "parts" and "%" are on a weight by weight basis, if nothing else is explicitly stated or evident for a skilled person in the specific context.

Thus, the process of the present invention is for the preparation of a compound of formula

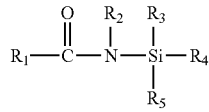

wherein $R_1$, $R_2$, $R_3$, $R_4$ and $R_5$ independently of each other represent $C_1$-$C_6$ alkyl, comprising reacting a compound of formula

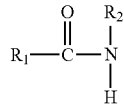

wherein $R_1$ and $R_2$ are as defined above with a compound of formula

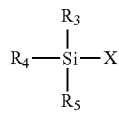

wherein X represents a halogen and $R_3$, $R_4$ and $R_5$ are as defined above in the presence of an organic base [OB] to form the compound of formula I and the salt of the protonated organic base [OB]H$^+$X$^-$, wherein X is as defined above and separating the compound of formula I from the salt of the protonated organic base [OB]H$^+$X$^-$, wherein the process is carried out in a reaction medium which consists essentially (at least 90%) of the compound of formula II, the compound of formula III, the organic base [OB] and the reaction products formed during the reaction and wherein 0.8 to 4 moles of the organic base [OB] are used per mole of the compound of formula II.

According to the invention, the organic base [OB] assists in deprotonating the compound of formula II

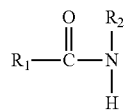

and then forms a salt with the anion X$^-$ from the compound of formula III. Therefore, it is not necessary to use the organic base [OB] in a large excess (like in those prior art processes in which an organic base [OB] is used as a solvent for the reaction components). To the contrary, it is preferred not to use the base in a large excess, because excess base has to be removed after the reaction, which makes the process less economic and less environmentally friendly. From a practical point of view not more than 4 moles of organic base [OB] are used per mole of the compound of formula II. Preferably, 0.8 to 2 moles of the organic base [OB] are used per mole of the compound of formula II, more preferably 0.9 to 1.5 moles and most preferably about 1 mole of the organic base [OB] is used per mole of the compound of formula II.

The substituents $R_1$, $R_2$, $R_3$, $R_4$ and $R_5$ are independently of each other $C_1$-$C_6$ alkyl, preferably $C_1$-$C_4$ alkyl, more preferably $C_1$-$C_2$ alkyl. "Alkyl" can be straight chain or branched or cyclic, where the number of carbon atoms allows for branched or cyclic groups. Substituents $R_1$, $R_2$, $R_3$, $R_4$ and $R_5$ can be identical or different. In a particularly preferred embodiment of the present invention the substituents $R_1$, $R_2$, $R_3$, $R_4$ and $R_5$ are the same, most preferably methyl.

In the present invention, the compound of formula III provides for the silyl group to be introduced into the compound of formula II in place of a hydrogen atom substituting the latter to form the compound of formula I. X in the compound of formula III is a leaving group and represents a halogen, preferably chlorine.

An organic base [OB] is present during the reaction to accept the hydrogen halide liberated in the reaction between the compound of formula II containing the substitutable hydrogen atom and the compound of formula III containing the leaving group X which represents a halogen and to form the corresponding salt [OB]H$^+$X$^-$. A nitrogen containing organic base is preferred as organic base [OB]. The concept of a nitrogen containing organic base is widely understood by the skilled person and is described in various textbooks. The nitrogen containing organic base is e.g. a compound of formula

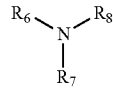

wherein $R_6$ to $R_8$ each represent a hydrocarbon group of usually not more than 10 carbon atoms, such as a straight, branched or cyclic alkyl, which is identical or different. Of course, it is also possible that two of the residues $R_6$ to $R_8$ are bonded together to form a ring structure of preferably 3 to 10, more preferably 4 to 8 carbon atoms with the nitrogen atom to which they are bonded.

Residues $R_6$ to $R_8$ can contain heteroatoms, e.g. one or two oxygen atoms. Preferably, residues $R_6$ to $R_8$ do not contain any heteroatoms. Examples of suitable organic bases [OB] are dicyclohexylmethylamine and dicyclohexylethylamine.

Preferably, residues $R_6$ to $R_8$ represent $C_1$-$C_4$ alkyl, such as in trimethylamine, triethylamine and tributylamine. Further examples are N,N-diisopropylethylamine and N-isopropyl-N,N-diethylamine. Triethylamine is particularly preferred. Alternatively, one or several of the residues $R_6$ to $R_8$ can also represent an aryl or heteroaryl with preferably less than 10 carbon atoms. The nitrogen containing organic base can also denote nitrogen containing heterocycles in the present invention, for example 5-7 membered heterocycles containing at least one nitrogen atom wherein the ring nitrogen or nitrogens may be unsubstituted or substituted by $C_{1-12}$ alkyl groups, such as pyridine, 4-(dimethylamino)pyridine, imidazole, N-methylmorpholine, N-methylpyrrolidine or pyrimidine. The nitrogen containing heterocycles can also be polycyclic, such as e.g. in aza- and diaza-bicylcic octanes, nonanes, undecanes and unsaturated derivatives thereof, for example 1,8-diazabicyclo-[5,4,0]undec-7-ene. In general, nitrogen containing organic bases are preferred which contain ≤20 carbon atoms. Mixtures of different organic bases can be used, as well, and are also denoted as organic base [OB] herein.

During the reaction according to the present invention a salt [OB]H$^+$X$^-$ is formed between the protonated organic base [OB]H$^+$ as defined above and the anion that results from the leaving group X. This salt can be removed from the reaction medium, and it is a particular advantage of the present invention that the process of the present invention allows for easy removal of the salt. In a particularly preferred embodiment of the present invention the salt [OB]H$^+$X$^-$ is precipitated from the reaction medium by adding an antisolvent to the reaction medium.

The antisolvent is not particularly restricted but of course the antisolvent should be inert to the components of the reaction medium and the salt [OB]H$^+$X$^-$ should not be soluble in the antisolvent. It is preferred to utilize an antisolvent with a boiling point sufficiently different from the boiling point of the final reaction product of formula I in order to allow easy separation of the antisolvent from the remaining mixture after removal of the precipitated salt [OB]H$^+$X$^-$. Particularly preferred, the antisolvent is thus an organic compound having a boiling point in the range of 35 to 100° C., more preferably in the range of 35 to 80° C.

In most cases, it has been shown that a nonpolar organic compound is particularly useful as antisolvent and alkanes having a boiling point in the above ranges are particularly preferred. According to the present invention, the antisolvent is preferably pentane or hexane. Hexane is most preferred. Other nonpolar organic solvents having a boiling point as indicated above can, however, also be used and in particular, organic compounds with a boiling point as defined above are useful. Apart from one antisolvent, mixtures of different antisolvents can also be used and mixtures of different antisolvents are also denoted as antisolvent herein.

The amount of antisolvent added to the reaction medium for precipitation of the salt [OB]H$^+$X$^-$ is not particularly limited. However, for economic reasons of course the amount of antisolvent should be kept as low as possible and generally it is sufficient to use 1 part antisolvent or less per part of reaction medium, but it is well possible to use more or less antisolvent if required.

Apart from the advantages described above, the omission of solvent when reacting the compound of formula II with the compound of formula III and the comparably small amount of antisolvent added for precipitation of the salt [OB]H$^+$X$^-$ allows to perform the novel process for the preparation of N-alkyl-N-trialkylsilylamides in smaller vessels than the processes described in the prior art. This is particularly favorable for industrial processes having an excellent productivity.

For the reaction of the compound of formula II with the compound of formula III, the compound of formula III is preferably added slowly to the compound of formula II and the organic base [OB] as the reaction may be rapid and exothermic. It is also possible to slowly add the compound of formula II to a container containing the compound of formula III and the organic base [OB]. Preloading the organic base [OB] in the reaction container together with one of the compounds of the formula II or III to which the other compound is added is preferred to reduce the volume to be added, but it is not required. Proper control of the temperature is facilitated when slowly adding together the compounds of formula II and III and the organic base [OB]. Depending on the particular embodiments of the compounds of the formula II and III and the organic base [OB], compounds for the formula II and III can also be mixed directly with the organic base [OB] or the compounds of formula II and formula III and the organic base [OB] may be combined in any possible sequence and rate of addition.

It is preferred that the process of the present invention is carried out under anhydrous conditions.

After combining all components, the reaction is then preferably left to take place for up to about 3 h, more preferably for up to about 2 h and most preferably for up to about 1 h. The reaction is believed to be sufficiently complete after the indicated time periods to balance a good yield of the desired product with a time efficient process. Depending on the particular embodiment of the compounds of the formula II and III and the organic base [OB] reaction times can also be shorter than 1 h and the reaction medium may also be directly worked up after the compound of formula II, the compound of formula III and the organic base are added together.

A preferred temperature for the reaction is between 10 to 50° C., more preferably between 20 to 50° C., particularly preferable is a temperature of about 30° C. Further preferred is a temperature for the reaction where the compounds of formula II and formula III as well as the organic base [OB] are liquid.

After the indicated time periods for the reaction to take place the reaction medium is preferably cooled whereby the reaction can be stopped. Cooling may also avoid the formation of undesired by-products and degradation of the desired product. Furthermore, cooling will facilitate precipitation of the salt formed between the protonated organic base as defined above and the anion that results from the leaving group. The reaction medium is preferably cooled to ≤10° C., more preferably ≤5° C. Usually the reaction medium is cooled to 0-5° C. If the salt [OB]H$^+$X$^-$ is removed by precipitation after addition of an antisolvent, it is preferred to add the antisolvent to the reaction medium after the reaction medium has been cooled to terminate the reaction.

After addition of the antisolvent, the salt [OB]H$^+$X$^-$ usually immediately precipitates, however, if required, the mixture containing the antisolvent can be further cooled, stirred or kept for some additional time to facilitate precipitation of the salt [OB]H$^+$X$^-$.

The precipitated salt [OB]H$^+$X$^-$ is preferably filtrated off and the filter cake is optionally washed with antisolvent. The antisolvent used for washing may be the same or different from the antisolvent used for precipitation of the salt [OB]H$^+$X$^-$. The amount of antisolvent used for washing should be kept as low as possible to result in a sufficient purity of the product while maintaining a good yield.

After the salt [OB]H$^+$X$^-$ has been removed (preferably by precipitation and filtration), the product of formula I is usually recovered by distillation. Particularly preferred is a fractional distillation under reduced pressure. Where the boiling point of the antisolvent used during precipitation and washing of the salt [OB]H$^+$X$^-$ is sufficiently below the boiling point of the desired compound of formula I it is preferred to strip off the antisolvent before the remaining mixture is subjected to further purification.

In an alternative embodiment, the salt [OB]H$^+$X$^-$ is not precipitated by addition of an antisolvent but the reaction medium still comprising the salt [OB]H$^+$X$^-$ is directly subjected to fractional distillation. However, while in this embodiment it is possible to omit the use of the antisolvent, generally, purity and yield of the desired product are improved, if the salt [OB]H$^+$X$^-$ is first removed (preferably by precipitation and filtration) before the desired product is isolated from the remaining mixture by fractional distillation.

In terms of the amounts of the different compounds used during the process according to the invention, the compound of formula II is reacted with the compound of formula III preferably in a compound of formula II/compound of formula III molar ratio of 1/5 to 5/1, preferably 1.5/1 to 1/1. Preferably about equimolar amounts of the compound of formula III and the organic base [OB] are used.

Another aspect of the invention relates to a process for manufacture of a peptide or peptide analogue, wherein in a first step a compound of formula I

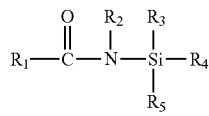

I is produced as described above and in a further step this compound is then reacted with an amino acid, a peptide or a peptide analogue in order to obtain a persilylated amino acid, peptide or peptide analogue which can then be further reacted with a compound of formula IV

Y-A-COOH    IV wherein Y is an amino protecting group, A is an amino acid, peptide or peptide analogue residue and COOH designates an optionally activated carboxylic group.

Processes in which a compound of formula I as defined above is reacted with a peptide or a peptide analogue (in the following sometimes denoted together as peptide (analogue)) or an amino acid in order to obtain a persilylated amino acid, peptide or peptide analogue and further reacting the persilylated amino acid, peptide or peptide analogue with a compound of formula IV

Y-A-COOH    IV wherein Y is an amino protecting group, A is an amino acid, peptide or peptide analogue residue and COOH designates an optionally activated carboxylic group are known in the prior art. In this connection it can be referred e.g. to EP 2 060 580 A1 or US 2010/0298537 A1 which explicitly disclose that process. It is explicitly referred to the disclosure of these documents regarding process details such as process conditions, solvents etc. of the process in which a compound of formula I as disclosed above is used for a preparation of persilylated amino acids, peptides or peptide analogues and in which such persilylated amino acids, peptides or peptide analogues are reacted with a compound of formula IV. The disclosures of EP 2 060 580 A1 and US 2010/0298537 A1 are included herein by reference.

Furthermore, the compound of formula IV and preferred definitions for residues Y and A and examples of the optionally activated residue COOH of formula IV are also disclosed in these documents and again it is explicitly referred to these document with regard to the corresponding preferred embodiments of residues Y, A and the optionally activated carboxylic group COOH.

Particularly preferred are processes, wherein X is as defined in paragraphs [0025] and [0026] of EP 2 060 580 A1, A comprises 4 to 15 amino acids, preferably as defined in paragraphs [0008], [0009], [0010], [0011], and [0012] of EP 2 060 580 A1 and the optionally activated carboxylic group is as defined in paragraphs [0028] and [0029] of EP 2 060 580 A1.

In addition to the persilylated peptides and peptide analogues containing from 4 to 15 amino acids as described in EP 2 060 580 A1 or US 2010/0298537 A1, persilylation of single amino acids, dimers or trimers of amino acids or of peptides and peptide analogues comprising more than 15 amino acids is also possible using the compound of formula I and subsequently reacting such persilylated derivatives with a compound of formula IV wherein A is an amino acid or peptide (analogue) residue.

The present invention thus also provides a process which comprises a) preparing a compound of formula I as described above, b) reacting the compound of formula I with an amino acid, a peptide or a peptide analogue to obtain a persilylated amino acid, peptide or peptide analogue and c) reacting the persilylated amino acid, peptide or peptide analogue with a compound of formula

Y-A-COOH    IV wherein Y is an amino protecting group, A is an amino acid, peptide or peptide analogue residue and COOH designates an optionally activated carboxylic group.

Step a) of this process is the process of the present invention as described above and below.

In step b) the persilylated amino acid, peptide or peptide analogue is obtained by silylating a corresponding amino acid or peptide (analogue) by reaction with the prepared compound of formula I, preferably in an organic solvent. The persilylated amino acid or peptide (analogue) can be isolated and purified if desired. It is however preferred to use the persilylated amino acid, peptide or peptide analogue in situ, e.g. by combining a solution containing persilylated amino acid, peptide or peptide analogue with a solution containing, optionally activated, compound of formula (IV) (step c)).

In the reaction of step b) generally 0.5 to 5 preferably 0.7 to 2 more preferably about 1 or 1 to 1.5 molar equivalents of the compound of formula I are used relative to the molar amount of functional groups to be silylated. Use of 2 to 4 molar equivalents of the compound of formula I relative to the molar amount of functional groups to be silylated is also possible. "Functional groups to be silylated" is understood to denote in particular groups having an active hydrogen atom that react with the compound of formula I, such as amino, hydroxyl, mercapto or carboxyl groups.

It is understood that "persilylated" intends to denote in particular an amino acid, a peptide or a peptide analogue in which the groups having an active hydrogen atom that can react with the compound of formula I are sufficiently silylated to ensure that a homogeneous reaction medium for coupling step c) is obtained.

The process steps of the process according to the present invention are generally carried out in the liquid phase.

When the silylation is carried out in the presence of a solvent said solvent is preferably a polar organic solvent more preferably a polar aprotic organic solvent. An amide-type solvent such as N,N-dimethylformamide or, in particular N,N-dimethylacetamide is more particularly preferred.

In another embodiment, silylation is carried out in a liquid silylation medium consisting essentially of the compound of formula I and amino acid, peptide or peptide analogue.

The example here after is intended to illustrate the invention without however limiting it.

EXAMPLE 1

In a reactor there were placed 1900 kg of triethylamine and 1510 kg of N-methylacetamide and mixed together. The temperature was maintained at about 30° C. and 2040 kg of trimethylsilyl chloride were added to the mixture of triethylamine and N-methylacetamide at a rate of 150 to 250 L/h. The reaction was then allowed to proceed for 1 h after the end of the addition of trimethylsilyl chloride. Then, the reaction medium was cooled to 0-5° C. and 3308 L of hexane were added to the reaction medium. The mixture was filtered to remove the precipitate of triethylamine hydrochloride. The resulting filter cake was washed once with 3138 L of hexane and once again with 1569 L of hexane. The filtrate and washings were combined and the low boiling hexane was stripped off. The mixture after having stripped off the hexane comprised about 75% N-methyl-N-trimethylsilylacetamide, about 20% N-methylacetamide and about 3% triethylamine. Some hexamethyldisiloxane formed by hydrolysis of trimethylsilyl chloride was also present. The crude residue was then submitted to a fractional distillation under reduced pressure in order to obtain the pure end product that was obtained in a yield of 70% and a purity of 99%.

The invention claimed is:

1. A process for the preparation of a compound of formula

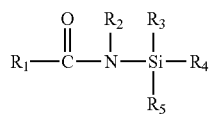

I wherein $R_1, R_2, R_3, R_4$ and $R_5$ independently of each other represent $C_1$-$C_6$ alkyl,
comprising
reacting a compound of formula

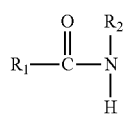

II wherein $R_1$ and $R_2$ are as defined above
with a compound of formula

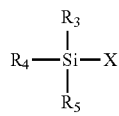

III wherein X represents a halogen and $R_3$, $R_4$ and $R_5$ are as defined above,
in the presence of an organic base [OB] to form the compound of formula I and the salt of the protonated organic base $[OB]H^+X^-$, wherein X is as defined above and separating the compound of formula I from the salt of the protonated organic base $[OB]H^+X^-$, wherein the process is carried out in a reaction medium, wherein the compound of formula II, the compound of formula III, the organic base [OB] and the reaction products formed during the reaction are present in a combined amount of at least 90% of the reaction medium,
and
wherein 0.8 to 2 moles of the organic base [OB] are used per mole of the compound of formula II.

2. The process according to claim 1, wherein about 1 mole of the organic base [OB] is used per mole of the compound of formula II.

3. The process according to claim 1, wherein $R_1, R_2, R_3, R_4$ and $R_5$ independently of each other represent $C_1$-$C_4$ alkyl which can be identical or different.

4. The process according to claim 3, wherein $R_1, R_2, R_3, R_4$ and $R_5$ independently of each other represent $C_1$ or $C_2$ alkyl which can be identical or different.

5. The process according to claim 1, wherein $R_1, R_2, R_3, R_4$ and $R_5$ are the same.

6. The process according to claim 5, wherein $R_1, R_2, R_3, R_4$ and $R_5$ represent methyl.

7. The process according to claim 1, wherein X represents chlorine.

8. The process according to claim 1, wherein the organic base [OB] is a nitrogen containing organic base.

9. The process according to claim 1, wherein the compound of formula I is separated from the salt of the organic base $[OB]H^+X^-$ by adding an antisolvent for $[OB]H^+X^-$ to the reaction medium so that the salt of the organic base $[OB]H^+X^-$ precipitates and can be removed by filtration.

10. The process according to claim 9, wherein the antisolvent is an alkane having a boiling point in the range from 35 to 80° C.

11. The process according to claim 1, wherein the compound of formula II is reacted with the compound of formula III in a compound of formula II/compound of formula III molar ratio of 1/5 to 5/1.

12. The process according to claim 1, wherein the reaction of the compound of formula II with the compound of formula III is carried out at a temperature in the range from 20 to 50° C.

13. A process for the manufacture of a peptide or peptide analogue which comprises
preparing a compound of formula I according to claim 1,
reacting the compound of formula I with an amino acid, a peptide or a peptide analogue to obtain a persilylated amino acid, peptide or peptide analogue, and
reacting the persilylated amino acid, peptide or peptide analogue with a compound of formula

Y-A-COOH    IV wherein Y is an amino protecting group, A is an amino acid, peptide or peptide analogue residue and COOH designates an optionally activated carboxylic group.

14. The process according to claim 1, wherein the organic base [OB] is triethylamine.

15. The process according to claim 1, wherein the compound of formula II is reacted with the compound of formula III in a compound of formula II/compound of formula III molar ratio of 1.5/1 to 1/1.

16. A process for the preparation of a compound of formula

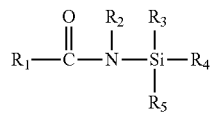

I wherein $R_1$, $R_2$, $R_3$, $R_4$ and $R_5$ independently of each other represent $C_1$-$C_6$ alkyl,
comprising
reacting a compound of formula

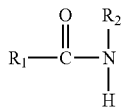
II wherein $R_1$ and $R_2$ are as defined above
with a compound of formula

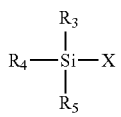
III wherein X represents a halogen and $R_3$, $R_4$ and $R_5$ are as defined above, in the presence of an organic base [OB] to form the compound of formula I and the salt of the protonated organic base [OB]H$^+$X$^-$, wherein X is as defined above and separating the compound of formula I from the salt of the protonated organic base [OB]H$^+$X$^-$, wherein the process is carried out in a reaction medium, wherein the compound of formula II, the compound of formula III, the organic base [OB] and the reaction products formed during the reaction are present in a combined amount of at least 90% of the reaction medium, and wherein about 1 mole of the organic base [OB] is used per mole of the compound of formula II, wherein about equimolar amounts of the compounds of formula III and the organic base [OB] are used and wherein compounds of formula II and III and the organic base [OB] are slowly added together.

17. The process according to claim 16, wherein the compound III is added at a rate of 150 to 250 L/h to the mixture of compounds II and of the organic base.

18. The process according to claim 16, wherein the compound II is added at a rate of 150 to 250 L/h to the mixture of compounds III and of the organic base.

* * * * *